US 11,457,859 B2

United States Patent
Knuebel

(10) Patent No.: US 11,457,859 B2
(45) Date of Patent: Oct. 4, 2022

(54) METHOD FOR DETERMINING A USER-SPECIFIC HAIR TREATMENT

(71) Applicant: Henkel AG & Co. KGaA, Duesseldorf (DE)

(72) Inventor: Georg Knuebel, Duesseldorf (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 942 days.

(21) Appl. No.: 16/314,995

(22) PCT Filed: Jul. 4, 2017

(86) PCT No.: PCT/EP2017/066574
§ 371 (c)(1),
(2) Date: Jan. 3, 2019

(87) PCT Pub. No.: WO2018/007354
PCT Pub. Date: Jan. 11, 2018

(65) Prior Publication Data
US 2019/0307392 A1 Oct. 10, 2019

(30) Foreign Application Priority Data

Jul. 5, 2016 (DE) ...................... 10 2016 212 202.9
Nov. 11, 2016 (DE) ...................... 10 2016 222 180.9

(51) Int. Cl.
| | |
|---|---|
| *A61B 5/00* | (2006.01) |
| *G16B 5/00* | (2019.01) |
| *G01N 21/3563* | (2014.01) |
| *G01N 21/359* | (2014.01) |
| *G01N 33/483* | (2006.01) |
| *G01N 33/52* | (2006.01) |
| *A61B 5/103* | (2006.01) |
| *A45D 44/00* | (2006.01) |

(52) U.S. Cl.
CPC ............ *A61B 5/448* (2013.01); *A61B 5/0075* (2013.01); *A61B 5/1032* (2013.01); *A61B 5/7246* (2013.01); *G01N 21/359* (2013.01); *G01N 21/3563* (2013.01); *G01N 33/4833* (2013.01); *G01N 33/52* (2013.01); *G16B 5/00* (2019.02); *A45D 2044/007* (2013.01); *A61B 2503/12* (2013.01)

(58) Field of Classification Search
CPC .......... A61B 5/448; A61B 5/0075; G16B 5/00
See application file for complete search history.

(56) References Cited

U.S. PATENT DOCUMENTS

| | | | |
|---|---|---|---|
| 2002/0010556 A1 | 1/2002 | Marapane | |
| 2003/0106564 A1* | 6/2003 | Olshavsky | ............... A61Q 5/08 132/207 |
| 2006/0281994 A1 | 12/2006 | Miyamae | |
| 2014/0118521 A1 | 5/2014 | Conti | |

FOREIGN PATENT DOCUMENTS

| | | |
|---|---|---|
| CN | 1440503 A | 9/2003 |
| JP | 2003344279 A | 12/2003 |
| JP | 2010112788 A | 5/2010 |
| WO | 0187245 A2 | 11/2001 |
| WO | 2015166403 A1 | 11/2015 |

OTHER PUBLICATIONS

M. Joy and D.M. Lewis, "The use of Fourier transform infra-red spectroscopy in the study of the surface chemistry of hair fibres", Nov. 19-20, 1990, International Journal of Cosmetic Science 13,249-261 (1991) (Year: 1991).*
EPO, International Search Report issued in International Application No. PCT/EP2017/066574, dated Oct. 6, 2017.

* cited by examiner

*Primary Examiner* — Hugh Maupin
(74) *Attorney, Agent, or Firm* — Lorenz & Kopf, LLP

(57) ABSTRACT

A method for determining a user-specific hair treatment by determining and inclusion of the degree of damage of hair is provided. To this end, initially, with the aid of near-infrared and/or infrared spectra of the keratin fibres of an individual, the amino acid oxidation product content is determined and a degree of damage is derived from it via a calibration model. Individual treatment advice that is based on the determined degree of damage is issued.

15 Claims, No Drawings

METHOD FOR DETERMINING A USER-SPECIFIC HAIR TREATMENT

CROSS-REFERENCE TO RELATED APPLICATION

This application is a U.S. National-Stage entry under 35 U.S.C. § 371 based on International Application No. PCT/EP2017/066574, filed Jul. 4, 2017 which was published under PCT Article 21(2) and which claims priority to German Application No. 10 2016 222 180.9, filed Nov. 11, 2016, which claims priority to German Application No. 10 2016 212 202.9, filed Jul. 5, 2016 which are all hereby incorporated in their entirety by reference.

TECHNICAL FIELD

The present disclosure relates to a method for determining a user-specific hair treatment.

BACKGROUND

When treating hair with cosmetic products, the effect of the product, for example the intensity of a colour, is greatly dependent on the degree of damage to the hair. In addition, damaged hair is often difficult to handle and dull.

Many different hair conditioning products are on the market which are intended to improve various properties or parameters of the hair such as gloss, for example. In many cases, however, the consumer does not know to what extent and in what manner their hair has been damaged. This might result in the user turning to products which are not very suitable for their particular case, and for them to be dissatisfied with the effect following its use.

Therefore, a determination of damage to the hair could be of great importance.

Hair can be damaged by processes which are natural or man made. The most important type of damage in this regard could be oxidative damage.

Examples of natural processes are a combined (for example simultaneous) action of UV light and oxygen ($O_2$) on the hair.

Examples of man-made processes in this regard may include the use of hair dyes (also known as colours), bleaching, and/or carrying out permanent waving.

During these, in addition to the desired cosmetic effects, such as lightening of the hair, for example, substantial damage to the hair may occur, for example when using oxidizing agents.

The likely origin of the damage process in this regard is the oxidation of amino acids, for example oxidation of the amino acids tryptophan, methionine, tyrosine, histidine and lysine which are present in the hair.

The oxidation of these amino acids can destroy the mechanical stability of the hair and even result in complete breakage of the hair if used multiple times. Furthermore, macroscopically detectable, for example sensory properties of the hair which can already be detected, for example surface roughness, could be impaired. In addition, the results of cosmetic treatments, in particular damaging processes, may be substantially altered even at an early stage of damage compared with a result for undamaged hair. Furthermore, grey hair could become yellowed.

Because the oxidation products of the cited amino acids are known, it is also possible to determine their content and thus the degree of damage to hair precisely.

In the academic and industrial arenas, a researcher or developer has access to a panoply of physical and chemical analytical methods for determining the degree of damage, for example a quantitative determination of the degree of oxidative damage.

In this regard, chromatographic methods are routinely used such as, for example, high performance liquid chromatography (HPLC), following a complicated acidic, basic or enzymatic hydrolytic digestion of the hair sample. Alternatively, colorimetric methods may be employed.

Moreover, all of these methods are complicated and require complex equipment, so that they cannot be accessed by an end user.

More and more consumers of products want a product that is tailored to their individual requirements. This is also particularly the case for beauty products such as skin and/or hair treatment agents.

BRIEF SUMMARY

Methods for determining an individualized hair treatment are provided. In an exemplarily embodiment, the method includes determining an amino acid oxidation product content of a plurality of samples of keratin fibres that have been damaged to various extents using a chromatographic or colorimetric method. Near-infrared and/or infrared spectra of the samples of keratin fibres that have been damaged to various extents is recorded. A calibration model that provides a correlation between the near-infrared and/or infrared spectra and the amino acid oxidation product content is generated. Near-infrared and/or infrared spectra of keratin fibres from an individual is recorded. A degree of damage of the keratin fibres from the individual is determined with aid of the calibration model. Individual treatment advice regarding the keratin fibres of the individual as a function of the determined degree of damage is issued. One or more amino acids associated with the amino acid oxidation product content are selected from the group of tryptophan, methionine, tyrosine, histidine, or lysine.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

Thus, one objective of the present disclosure is therefore a method for determining individual hair treatment advice which enables an end user to determine the amino acid oxidation product content in their hair in a simple manner and to obtain hair treatment advice which are tailored thereto.

This objective is achieved by employing a method for determining an individualized hair treatment, with the steps of:

a) determining an amino acid oxidation product content of a plurality of samples of keratin fibres that have been damaged to various extents, by employing a chromatographic or colorimetric method;

b) recording near-infrared and/or infrared spectra of the samples of keratin fibres that have been damaged to various extents;

c) generating a calibration model which provides a correlation between near-infrared and/or infrared spectra and an amino acid oxidation product content;

d) recording near-infrared and/or infrared spectra of the keratin fibres from an individual;
e) determining a degree of damage of the keratin fibres from this individual with the aid of the calibration model;
f) issuing individual treatment advice regarding the keratin fibres of the individual as a function of the determined degree of damage,
wherein the amino acids are selected from the group including of tryptophan, methionine, tyrosine, histidine and lysine.

The terms "keratin fibres" and "hair" as used in the context of this application encompass fur, wool and feathers, but in particular human hair. The terms "hair" and "keratin fibres" are used synonymously.

In the context of this application, a "user" or "consumer" may be the individual whose keratin fibres are being tested and for whom an individualized hair treatment is determined. Alternatively, a "user" or "consumer" may be a third party who is testing the keratin fibres of an individual and for whom an individualized hair treatment is being determined.

Near-infrared and/or infrared spectroscopy enables the amino acid oxidation product content to be determined in a direct, non-destructive manner without complicated sample preparation and without the analysis changing or destroying the structure of the hair. This has the advantage that the result is obtained very quickly and a treatment can be undertaken immediately after determining the oxidation product content. A further advantage is that the near-infrared and/or infrared spectroscopy can be carried out on keratin fibres which are on an individual's head.

Direct oxidation products of tryptophan include 5-hydroxytryptophan and oxindolylalanine (2-hydroxytryptophan). Further oxidation products are formed by cleavage of the indole ring: N-formylkynurenine, kynurenine and hydroxykynurenine. Yet more oxidation products are formed by fresh cyclization: carbolines and hexahydropyrroloindole.

In a preferred embodiment as contemplated herein, the oxidation product of an amino acid is selected from the group including of 5-hydroxytryptophan, oxindolylalanine, N-formylkynurenine, kynurenine, hydroxykynurenine, carbolines and hexahydropyrroloindol.

The oxidation products of methionine include methionine sulphoxide (2-amino-4-(methylsulphinyl)butanoic acid) and/or methionine sulphone.

In a preferred embodiment as contemplated herein, the amino acid oxidation product is selected from the group including of methionine sulphoxide and methionine sulphone.

The claimed method initially requires the generation of a calibration model. To this end, in a step a), the amino acid oxidation product content of a plurality of samples of keratin fibres which have been damaged to varying extents is determined by employing a chromatographic method, for example HPLC, or a colorimetric method.

In a step b), near-infrared and/or infrared spectra of the samples of keratin fibres which have been damaged to varying extents are recorded.

The near-infrared (NID) and/or infrared (IR) spectra may, for example, be obtained by employing ATR ("attenuated total reflection") (near) infrared spectroscopy.

In step c), a calibration model is generated which produces a correlation between the near-infrared and/or infrared spectra of the samples (calibration spectra) and the amino acid oxidation product content of the samples which has been determined by employing an independent chromatographic or colorimetric method. Generating the calibration model may also include recording, for the majority of the calibration hair samples, a calibration spectrum of at least a portion of the near-infrared and/or infrared light which is reflected and/or scattered from the calibration hair samples during exposure of the calibration hair samples to near-infrared and/or infrared light, and determining a degree of damage of the calibration hair samples by employing an independent chromatographic or colorimetric method, assigning a degree of damage to the calibration spectrum and determining a correlation between the majority of the calibration spectra and the majority of the degrees of damage is determined.

The steps a) and b) do not necessarily have to be carried out one after the other and in this order. Thus, step b) may be carried out first, followed by step a).

In a preferred embodiment, the calibration model from steps a) to c) is provided as information stored on a local data carrier or in a cloud. A "local data carrier" in the context of this application includes any physical carrier substances on which data can be held. In a particularly preferred embodiment, the data carrier is identical to the data processing device to which the (N)IR spectrometer is connected in order to record near-infrared and/or infrared spectra of the keratin fibres. This may in particular be a smartphone, a tablet, a laptop or a computer. In an alternative embodiment, the calibration model from steps a) to c) is provided as stored information in a cloud.

By using mathematical models, and by employing measurement of calibration hair samples which comprise an amino acid oxidation product content determined by employing a known analytical method, a mathematical model can be generated which then means that an amino acid oxidation product content of a hair sample, also known as a braid, from the consumer can be calculated with the aid of the recorded NIR or IR spectra, and hence the damage to the hair can be calculated. An analysis of the spectrum and a use of the model can then, for example (with suitable apps) be carried out by employing known data processing devices such as smartphones, tablet, or the like.

The mathematical model may be an artificial system which, for example, learns from the calibration hair samples and which can then be generalized after the end of the learning phase. This means that not only are the examples memorized, but patterns and legitimacies in the learning data are recognized. In this regard, different strategies can be pursued. As an example, supervised learning, semi-supervised learning, unsupervised learning, reinforcement learning and/or active learning may be employed, in particular in connect with deep learning methods. Supervised learning may, for example, be carried out by employing an artificial neural network (approximates to a recurrent neural network) or by employing a Support Vector Machine. Unsupervised learning may also be carried out by employing an artificial neural network (for example an autoencoder), for example.

In order to optimize the calibration model, further factors, in particular categorical factors, such as the ethnicity of the individual, the age of the individual (as a category or metric), the hair colour of the individual (as a category or metric) may be taken into consideration.

Further on in the method, in step d), a near-infrared and/or infrared spectrum of the keratin fibres of an individual is recorded. This may, for example, be carried out in a manner such that during exposure of a hair sample of the individual with near-infrared and/or infrared light, a spectrum of at least a portion of the near-infrared and/or infrared light which is reflected and/or scattered from the hair sample is recorded. Preferably, in step d), a plurality of near-infrared and/or infrared spectra per measuring point is recorded and respectively averaged.

In step e), the degree of damage of the keratin fibres of the individual is determined with the aid of the calibration model generated in steps a) to c).

To this end, for example, at least a portion of the near-infrared and/or infrared spectrum from the hair of the individual is compared with the calibration model and a degree of damage of the hair is determined/assigned.

In a further advantageous embodiment, the near-infrared and/or infrared spectra of the keratin fibres of an individual are recorded at different positions along the keratin fibres. Thus, the near-infrared and/or infrared spectra may be recorded at the root and/or in the centre and/or at the ends of the keratin fibres. A corresponding characteristic degree of damage can then be determined for each of these positions.

Like other vibrational spectroscopies, near-infrared spectroscopy is based on the excitation of molecular vibrations by electromagnetic radiation in the (near) infrared range. In near-infrared spectroscopy, detection is carried out in the near infrared (from about 760 to about 2500 nm or approximately 13000-4000 $cm^{-1}$). Herein below, for light with a wavelength in the range from about 12500 to about 4000 $cm^{-1}$, the term "near-infrared" (NIR) will be used, and for light with a wavelength in the range from about 3999 to about 400 $cm^{-1}$, the term "infrared" (IR) will be used.

By using miniaturized (N)IR spectrometers and/or (N)IR sensors as well as linking them to a mobile data processing device, the method and in particular step d) of the method can, for example, be carried out by the private individual themselves, by any person at a point of sale (POS) of hair treatment agents, or by a hairdresser. In a preferred embodiment, the mobile data processing device is a smart device, for example a smartphone, a tablet or a laptop.

The (N)IR spectrometers may in particular also be provided in the mobile form, for example in the form of handheld spectrometers or add-on spectrometers.

An example of a suitable handheld spectrometer is the "MicroNIR OnSite" from Viavi Solutions Inc. This spectrometer is supplied with current and controlled from a tablet or a laptop via a USB connection. This handheld spectrometer, with a measuring time of between about 0.25 and about 0.5 seconds, allows near-infrared and/or infrared spectra of the keratin fibres of an individual to be recorded in real time. The spectrometer has two integrated vacuum-tungsten lamps and an InGaAs photodiode array with 128 pixels. The "MicroNIR OnSite" operates in a wavelength range of about 6060 to about 10526 $cm^{-1}$. The distance between the keratin fibres and the glass of the handheld spectrometer may be between 0 and about 15 mm, wherein a distance of about 3 mm is preferred.

In one embodiment as contemplated herein, the entire method for determining an individualized hair treatment is carried out by the tablet or the laptop which supplies the "MicroNIR OnSite" spectrometer with current and controls it. Alternatively, the spectroscopic data obtained could be sent to a further (mobile) data processing device, in particular a further smart device, which then carries out the method for determining an individualized hair treatment. Transmission of the spectroscopic data may, for example, be carried out wirelessly by WLAN (WiFi) or Bluetooth.

A further suitable handheld spectrometer is the "i-Spec Nano" from B&W Tek. The spectrometer is supplied with current via a USB connection and a (mobile) data processing device connected thereto or via a battery. The spectrometer has a light source and operates in a wavelength range of about 4545 to about 7692 $cm^{-1}$. Transmission of the spectroscopic data to a (mobile) data processing device which then carries out the method for determining an individualized hair treatment may be carried out wirelessly via WLAN (WiFi) or Bluetooth.

The handheld spectrometer "QualitySpec Trek" from ASD Inc is also suitable. This operates in a wavelength range of about 28571 to about 400 $cm^{-1}$.

A further handheld spectrometer is the "SCiO" by Consumer Physics, which displays the spectroscopic data on a smart device with the aid of the integrated "SpectroScan" app. The handheld spectrometer operates in the short wavelength range of the NIR and in fact at wavelengths of about 9090 to about 14285 $cm^{-1}$ (corresponds to about 700 to about 1100 nm). The evaluation of the measured data is carried out with the aid of a cloud in which, for example, a material database, chemometric models and algorithms are stored.

Still other suitable handheld spectrometers are available from Attonics Systems, which operate either in a wavelength range of about 9090 to about 26315 $cm^{-1}$ (VIS-NIR) or of about 3333 to about 10000 $cm^{-1}$ (NIR). These spectrometers are based on interferometers and have a high light throughput and a high spectral resolution (<about 5 nm for VIS-NIR spectrometers and <about 20 nm for the NIR spectrometer). The spectrometers have a multi-phase shift array (MPA) chip and an optical array in a circular tube. Furthermore, the spectrometers are compatible with mobile data processing devices.

A further suitable miniaturized NIR spectrometer is integrated into the H2 smartphone from Changhong.

Further examples of VIS-NIR spectrometers are the miniature spectrometers "USB2000-VIS-NIR" and "USB4000-VIS-NIR" from Ocean Optics. This spectrometer operates with a wavelength range of about 350 to about 1000 nm. The spectrometers are linked to a data processing device via an USB connection.

In addition, a series of NIR sensors or NIR evaluation modules exist which can be used in handheld spectrometers. Suitable NIR evaluation modules are the "DLP® NIRscan" and "DLP® NIRscan Nano" modules from Texas Instruments. These have two tungsten lamps and InGaAs photodiodes as the detectors. The "DLP® NIRscan" module operates in the wavelength range of about 4016 to about 7407 $cm^{-1}$, and the "DLP® NIRscan Nano" module operates in the range from about 5882 to about 11111 $cm^{-1}$. Communication of the spectroscopic data is carried out wirelessly via Bluetooth Low Energy. With the aid of "Software Developer Kits" (SDK), for example the Open Source SDK from KST Technologies, apps can be developed which evaluate or further process the spectroscopic data.

Further suitable NIR sensors are obtainable with the designation "NeoSpectra" from Si-Ware Systems. Specific sensors include: NeoSpectra SW62221-1.7, NeoSpectra SW62221-2.1 and NeoSpectra SW62221-2.5, which operate in different wavelength ranges.

In a preferred embodiment, step d) is controlled by a mobile data processing device, in particular a smart device. In this regard, the method is preferably controlled by a pre-installed app on the smart device. Smart devices in particular include smartphones or tablets.

The term "app" in the context of this application designates a computer program which is used to process or support a feature which is not system-engineered. The term "app" in particular comprises application software for smart devices such as smartphones and tablets ("mobile app"), as well as desktop application software. The app may be a native app which only functions on a platform, or a platform-independent web, hybrid or cross-platform app.

Particularly preferably, the app can be downloaded via a QR code, a NFC chip, a barcode or a RFID chip directly by the hairdresser or at a point of sale (POS) of hair treatment agents.

Alternatively, in particular in the case in which it is to be installed on a smart device, the app can be downloaded via an internet sales platform integrated into the respective operating system of the smart device. In the case of a smart device with the "Apple iOS" operating system, this may, for example, be the "App Store", or in the case of a smart device with the "Android" operating system, this may be the "Google Play Store".

In one embodiment, the QR code, the NFC chip, the barcode or the RFID chip contains a web link which directs the user of the method to a website from which the user of the method can download the app.

It is more preferable for the degree of damage determined in the method to be output as a "% damage" or in relative terms ("very severe, severe, average, slight and none at all"). An output in "% damage" enables a direct comparison to be made of the degrees of damage determined at different times for a particular individual. Thus, for example, the effectiveness of the treatment can be followed over time.

The degree of damage may be issued optically, for example by employing a display device on the (mobile) data processing device, or acoustically, for example by employing a voice message via a loudspeaker.

In a particularly preferred embodiment of the method, the individual treatment advice comprises a recommendation of bleaching agents and/or hair colorants and/or hair conditioning products and/or hair styling agents.

In this regard, the recommendation may be a display or message stating a specific product name of a bleaching agent and/or hair colorant and/or hair conditioning product and/or hair styling agent. Alternatively, the recommendation may comprise a display or message naming a product line or series, in particular a bleaching agent line/series and/or hair colorant line/series and/or hair conditioning product line/series and/or hair styling line/series from a manufacturer.

In an alternative embodiment of the method, the individual treatment advice includes a recommendation to avoid bleaching and/or oxidative colouring and/or permanent shaping and/or heat treatments for a specific period of time. This individual treatment advice may in particular be given when a specific percentage for the determined degree of damage is exceeded or when the relative categorization of the degree of damage is in the ranges "very severe" and/or "severe".

The term "permanent shaping" encompasses all methods for curling straight hair or straightening curly hair. These may be permanent waving methods or chemical straightening methods. In addition to the use of chemicals, heat treatments may also damage keratin fibres even more. Accordingly, the individual treatment advice may comprise the recommendation to avoid heat treatments such as, for example, the use of curling tongs or straighteners, for a specific period of time.

If, for example, the keratin fibres exhibit a slight to average degree of damage, then in a further, preferred embodiment as contemplated herein, the individual treatment advice may comprise the recommendation to only lighten the hair colour and/or to colour it oxidatively by a maximum number of shades for a specific period of time.

In a further embodiment as contemplated herein, the individual treatment advice may include a dosage recommendation for bleaching and/or oxidative colouring and/or a prediction of the result of bleaching and/or oxidative colouring.

When bleaching or oxidatively colouring keratin fibres, in an alkaline medium the cuticle layer of the keratin fibres is opened up and a hydrogen peroxide cocktail—in a dose which varies as a function of the desired bleaching or lightening result—releases the natural (coloured) pigments to a greater or lesser degree. The higher the hydrogen peroxide dose, the lighter will the keratin fibres become. This mode of action means that bleaching or oxidative colouring always damages keratin fibres in a detectable manner. The higher the concentration of the hydrogen peroxide and the longer the reaction time, the more severe the damage.

When the keratin fibres have already been damaged, then, it is advantageous to lighten the hair colour and/or to oxidatively colour the hair by only a maximum number of shades for a specific period of time. Similarly, when the keratin fibres have already been damaged, it is advantageous to limit the concentration of hydrogen peroxide to a recommended dose in order to avoid/reduce further (severe) damage by the bleaching or colouring process.

Before carrying out bleaching or (oxidative) colouring, more and more users want to have a realistic impression of how their hair will look after bleaching or (oxidative) colouring. Many purveyors of bleaching or (oxidative) colours thus offer colour advice apps. The "Schwarzkopf Frisuren Styleguide" [Schwarzkopf Hair Style Guide] app, for example, enables hair colours to be tested in advance in real time. To this end, the user loads the app onto a smart device and takes a photo of their head with the front camera. The software of the app recognizes the face and shape of the head. The user then selects a specific bleaching product or (oxidative) colouring product and receives on the display equipment of the smart device how he/she will look after carrying out this bleaching or (oxidative) colouring.

In order to predict the bleaching or colour result, firstly, the initial hair colour is determined and then the bleaching or colouring result is calculated, based on the specific bleaching or colouring product selected by the user. Because the degree of damage of hair has an influence on the bleaching or colouring result, in order to determine an individualized hair treatment better, the method in particular delivers more realistic predictions of a result of bleaching and/or (oxidative) colouring. Preferably, the method for determining an individual hair treatment is a component of a colour advice app.

The individual treatment advice may also include determining the chemical composition of a hair treatment agent, in particular a bleaching agent, a hair colorant, a hair conditioning product and/or a hair styling agent.

In a further advantageous embodiment of the method, the individual treatment advice includes encouraging or discouraging the individual from using hair treatment products which the user of the method identifies with the aid of QR codes, NFC chips, barcodes or RFID chips.

In this embodiment of the method, after determining the degree of damage, the user of the method, for example a hairdresser or any person at the point of sale of hair treatment agents, can determine suitable or unsuitable hair treatment agents via QR codes, NFC chips, barcodes or RFID chips which, for example, are applied to the hair treatment agent itself or at the storage site thereof, for example on a shelf at the hair salon or at the point of sale of hair treatment agents.

QR codes, NFC chips, barcodes or RFID chips allow information to be transmitted wirelessly.

The term "barcode" means an optoelectronically readable script which is made up of various broad, parallel stripes and gaps. The data in a barcode are input by machine with optical reading devices such as, for example, barcode reader devices (scanners) or cameras, and processed further electronically. Many smart devices comprise software which enables acquisition using the digital camera of the smart device and display of the code information immediately to the user in a decoded form.

A QR ("quick response") code is a two-dimensional code which includes a quadratic matrix of black and white squares which represents the coded data in a binary manner Usually, smart devices have a built-in camera. After photographing the QR code, the QR code is read out/interpreted with the aid of software.

NFC chips and RFID chips are transmitter-receiver systems. In this case, at least one communication partner must be active, i.e. must initiate the communication. The other partner may, for example, be a chip without an energy supply. This passive part is also known as a transponder (=transmitter & responder). In addition to active-passive communication between, for example, a smart device as the active communication partner and a transponder/chip, active communication is also possible.

The coupling/excitation occurs by employing magnetic oscillating fields produced by the active communication partner with a short range, or by high frequency radio waves. In this manner, not only is data transmitted, but the transponder is also supplied with energy. The active communication partner, for example a smart device, contains a piece of software which controls the actual reading process, and what is known as middleware with interfaces to further (mobile) data processing devices and/or databases.

RFID ("radio frequency identification") functions via radio waves. The RFID technology covers a very wide range of different chips and reading devices which essentially differ in their storage capacity, production process, price, frequency range and range.

NFC ("near field communication") is a standardized specialization of the RFID technology, which was developed especially for data transmission over short distances (max. 10 cm).

QR codes, NFC chips, barcodes or RFID chips may, for example, contain information regarding which hair treatment agents are suitable or unsuitable for associated degrees of damage.

In an alternative embodiment of the method, the individual treatment advice includes advising the individual as to the use of bleaching agents and/or colorants and/or care products which are individually manufactured for the individual, and to instigate an ordering procedure, preferably by calling up a website of a manufacturer of individual bleaching agents and/or individual colorants and/or individual care products.

More and more clients want a product that is individually tailored to their needs. In this regard, it could be a product that is specially manufactured for the client or what is known as a "mass customized" product. In a "mass customized" product, by varying a few features of a product which are nevertheless seen by the client as important, individualization is obtained. Preferably, these "mass customized" products are based on the concept of modularization, i.e. the product may be composed of various individual modules/components.

Between the many features/ingredients of a product there are often many dependencies which can be expressed as "Do's" or "Don'ts". In order to obtain a unique product definition, it may be advantageous for the ordering procedure to run with the aid of a product configurator. This configurator helps the client with the choice of features/ingredients and advises them on permissible/non-permissible combinations of features, wherein the latter cannot be selected.

In bleaching agents, colorants, care products and styling agents for keratin fibres, the relevant product features in particular include the chemical ingredients of the agent, the physical properties of the agent and the type of formulation of the agent. As an example, with the aid of a product configurator, the selection of chemical and/or physically incompatible ingredients or the selection of ingredients which are unsuitable for the determined degree of damage can be avoided. In contrast, the selection of suitable ingredients for the determined degree of damage can be highlighted or suggested by the product configurator.

It is also preferable for the individual treatment advice to be stored and used in subsequent methods for a long-term recommendation(s).

In a further embodiment, prior to issuing the treatment advice/recommendation to the user, a data reconciliation is carried out between the (mobile) data processing device, in particular between the smart device and data which is stored in a cloud. This may, for example, be data from users with identical or similar degrees of damage, gender, age, behaviour patterns as well as, optionally, further identical or similar keratin fibre parameters and the recommendations/measures derived therefrom. By recording empirical data, for example as regards a successful treatment, other users can confirm or change an assessment of the suitability of a piece of treatment advice/recommendation. This means that the user will always receive an optimized recommendation.

In various exemplary embodiments, the individual treatment advice may comprise the recommendation that a hairdresser be sought out. In various exemplary embodiments, a booking procedure can be instigated directly via the software/app which determines the individual treatment advice. In this regard, for example, the contact details of hairdressers may be stored in the software/app and displayed to the user. In addition, the selection can be limited by employing filters such as the postcode, for example. In various exemplary embodiments, an appointment can be made directly via the software/app. Alternatively, a hairdresser's appointment could be booked via a separate piece of software/app such as Treatwell, for example.

In an advantageous embodiment, the method is not carried out on the basis of the amino acid oxidation product content, but on the basis of the content of two or more amino acid oxidation products.

In a particularly preferred embodiment, in addition to the degree of damage of the keratin fibres, their curl is determined and this is taken into consideration in the individual treatment advice.

In another preferred embodiment, in addition to the degree of damage of the keratin fibres, their thickness is determined and this is taken into consideration in the individual treatment advice.

In addition to the degree of damage of the keratin fibres, other properties of the keratin fibres influence the success of a treatment of the keratin fibres. Thus, in particular, the curl and/or thickness of keratin fibres may have an influence on the outcome of a treatment of the keratin fibres. The curl and/or thickness of keratin fibres has a particular influence on the treatment of keratin fibres with conditioning agents. Because a successful treatment with conditioning products is desirable, in particular for previously damaged keratin fibres, taking the curl and/or the ethnicity into consideration in the individual treatment advice is particularly advantageous.

The values for the curl and/or thickness of keratin fibres may, for example, be determined using suitable methods via the smart device on which the method is carried out.

Hair curl may, for example, be determined with the aid of image processing and image processing methods. To this end, the user of the method photographs at least a portion of the hair of the individual. Suitable image processing and image processing programs such as "ImageJ" determine the linear fraction in the image, with the aid of suitable plug-ins. Straight hair results in a high linearity fraction; very curly hair results in a small linearity fraction. The degree of curl can preferably be given as the "% curl".

The image processing and image processing program for determining the curl may be a component of the app for carrying out the method for individualized hair treatment. Alternatively, curl determination may be carried out with the aid of image processing and image processing methods by employing the separate methods. Advantageously, the separate method is carried out via an app which is loaded onto the mobile data processing device, in particular the smart device, which is used to carry out the method for individualized hair treatment.

Curl determination may be carried out via separate methods which are not linked to the method for determining an individualized hair treatment, or in fact it may be carried out empirically.

The information regarding curl may be provided via a suitable interface, for example a dialogue box which opens the smart device when carrying out the method for individualized hair treatment. The dialogue box may in this regard have relative degrees of curl such as, for example "none at all", "slight", "gentle", "average", "strong" and "very strong", and the user of the method selects the subjectively determined curl. In the case of a percentage curl determined via a separate method, a specific numerical value, for example "20%" may be entered.

The thickness may, for example, be determined with the aid of an accessory for smart devices. An example in this regard is a microscope add-on which is clamped over the lens of the smart device. Examples of microscope add-ons for smart devices of this type are the "Nurugo Micro" from Nurugo or "µPeek" from Scrona. Before or after recording the near-infrared and/or infrared spectra of the keratin fibres of the individual (step d), the user of the method also determines the thickness of the keratin fibres of the individual. To this end, with the aid of a microscope add-on, they will photograph from about 2 to about 20, preferably from about 3 to about 15 and particularly preferably from about 5 to about 10 different keratin fibres together with a scale reference. The average hair thickness for the individual is determined using evaluation software which may be integrated into the app for carrying out the method for individualized hair treatment.

A further alternative method for determining the hair thickness which can be carried out with suitable accessories via a smart device involves the deflection of laser light.

The hair thickness may be determined via separate methods which are not part of the method for determining an individualized hair treatment, or may be carried out empirically.

The information regarding the hair thickness may be provided via a suitable interface, for example a dialogue box which opens on the smart device when carrying out the method for individualized hair treatment. The dialogue box here may provide relative hair thicknesses such as "fine", "normal" and "thick", for example, and the user of the method selects the subjectively determined hair thickness. In the case of an absolute hair thickness determined via a separate method, a numerical value, for example 80 µm, may be entered.

Thick hair and (very) curly hair require hair conditioning products with a high proportion of fat or oil-containing ingredients for optimal care, while hair conditioning products with a low proportion of fat and/or oil-containing ingredients are advantageous for thin and/or straight hair.

The use of hydrogen peroxide in a highly alkaline medium during bleaching and oxidative colouring leads in most cases to a (further) damage to the keratin fibres treated in this manner. In order to avoid or reduce damage, agents for bleaching and/or for oxidative colouring frequently also contain conditioning products.

In a particularly preferred embodiment as contemplated herein, as a function of the determined degree of damage and as a function of the thickness and/or the curl, the individual treatment advice comprises a recommendation of bleaching agents and/or hair colorants and/or hair conditioning products and/or hair styling agents with a content of fat or oil-containing ingredients that is tailored to the degree of damage and the thickness and/or curl of the keratin fibres.

Fat and oil-containing ingredients in particular include glycerine mono-, di- or tri-esters with fatty acids, fatty acids, fatty alcohols, fatty acid mono- or di-esters with fatty alcohols, vegetable oils, mineral oils, natural waxes and synthetic waxes.

A further important property of keratin fibres which influences the result of a treatment of keratin fibres is the grey content. The grey content of keratin fibres in particular has an effect on the result of bleaching or an oxidative colouring process.

The grey content may be determined via separate methods which are not linked to the method for determining an individualized hair treatment, or it may also be determined empirically.

As an example, the grey content may be determined with the aid of image processing and image processing methods. To this end, the user of the method photographs at least a portion of the keratin fibres of the individual. Preferably, the photographed portion of the keratin fibres contains white parts of the roots. Suitable image processing and image processing programs determine the grey content in the image. In a particularly preferred embodiment, the determination of the grey content is an integral component of the method for individualized hair treatment and will be carried out by the app which carries out the method for determining an individualized hair treatment.

The information regarding the grey content may be provided via a suitable interface, for example a dialogue box which opens on the smart device when carrying out the method for individualized hair treatment. The dialogue box may in this case display percentages of grey content such as, for example, "10%", "30%", "50%", "70%", "90%" and "100%", and the user of the method selects the subjectively determined grey content. In the case of a percentage grey content determined via a separate method, a numerical value, for example "68%", may be entered.

Grey hair usually takes up the oxidative dye precursors used in oxidative colouring less well than pigment-rich hair. Depending on the grey content, this leads to different colour results.

In individuals with (very) severely damaged hair and no or only a low grey content, then, the individual treatment advice may be to discourage the individual from using bleaching and/or colorants and to use colours without oxidative treatment, for example toners or intense toners.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A method for determining an individualized hair treatment, the method comprising the steps of:
   a) determining an amino acid oxidation product content of a plurality of samples of keratin fibres that have been damaged to various extents using a chromatographic or colorimetric method;
   b) recording near-infrared and/or infrared spectra of the samples of keratin fibres that have been damaged to various extents;
   c) generating a calibration model that provides a correlation between the near-infrared and/or infrared spectra and the amino acid oxidation product content;
   d) recording near-infrared and/or infrared spectra of keratin fibres from an individual;
   e) determining a degree of damage of the keratin fibres from the individual with aid of the calibration model;
   f) issuing individual treatment advice regarding the keratin fibres of the individual as a function of the determined degree of damage,
   wherein one or more amino acids associated with the amino acid oxidation product content are selected from the group of tryptophan, methionine, tyrosine, histidine, or lysine.

2. The method of claim 1, wherein the calibration model from steps a) to c) is provided as stored information on a local data carrier or in a cloud.

3. The method of claim 1, wherein step d) is carried out by a hairdresser, at a point of sale (POS) of hair treatment agents or privately.

4. The method of claim 1, wherein step d) is carried out by a smart device.

5. The method of claim 1, wherein the degree of damage is output as "% damage" or in relative terms.

6. The method of claim 1, wherein the calibration model takes into consideration ethnicity of the individual, age of the individual and/or hair colour of the individual.

7. The method of claim 1, wherein the individual treatment advice includes a recommendation of bleaching agents, hair colorants, hair conditioning products, and/or hair styling agents.

8. The method of claim 1, wherein the individual treatment advice includes the recommendation to desist from bleaching and/or oxidative colouring and/or permanent shaping and/or heat treatment for a specific period of time.

9. The method of claim 1, wherein the individual treatment advice includes a dosage recommendation for bleaching, oxidative colouring, and/or a prediction of a result of bleaching and/or oxidative colouring.

10. The method of claim 1, wherein the individual treatment advice includes encouraging or discouraging the individual from using hair treatment products that a user of the method identifies with the aid of QR codes, NFC chips, barcodes or RFID chips.

11. The method of claim 1, wherein the individual treatment advice includes encouraging the individual to use bleaching agents, hair colorants, hair conditioning products, and/or hair styling agents that are individually manufactured for the individual and to instigate an ordering procedure.

12. The method of claim 1, wherein the individual treatment advice includes determining a chemical composition of a hair treatment agent.

13. The method of claim 1, wherein curl of the keratin fibres of the individual is determined and taken into consideration in the individual treatment advice.

14. The method of claim 1, wherein thickness of the keratin fibres of the individual is determined and taken into consideration in the individual treatment advice.

15. The method of claim 1, wherein grey content of the keratin fibres of the individual is determined and taken into consideration in the individual treatment advice.

* * * * *